United States Patent [19]
Navab

[11] Patent Number: 5,923,727
[45] Date of Patent: Jul. 13, 1999

[54] METHOD AND APPARATUS FOR CALIBRATING AN INTRA-OPERATIVE X-RAY SYSTEM

[75] Inventor: Nassir Navab, Erlangen, Germany

[73] Assignee: Siemens Corporate Research, Inc., Princeton, N.J.

[21] Appl. No.: 08/940,923

[22] Filed: Sep. 30, 1997

[51] Int. Cl.$^6$ ................................................. A61B 5/05
[52] U.S. Cl. ............................................. 378/207; 378/63
[58] Field of Search .................................. 378/20, 62, 63, 378/204, 205, 206, 207

[56] References Cited

U.S. PATENT DOCUMENTS

| | | | |
|---|---|---|---|
| 5,315,630 | 5/1994 | Sturm et al. | 378/205 X |
| 5,446,548 | 8/1995 | Gerig et al. | 378/205 X |
| 5,588,430 | 12/1996 | Bova et al. | 378/204 X |
| 5,772,594 | 6/1998 | Barrick | 378/205 X |

*Primary Examiner*—David P. Porta
*Attorney, Agent, or Firm*—Adel A. Ahmed

[57] ABSTRACT

Apparatus for calibrating an intra-operative X-ray system having an X-ray source and a detector includes an optical camera associated with the X-ray source; an optical camera associated with the detector; an X-ray phantom placed within a field of view of the X-ray system during an off-line process; an optical phantom placed within a field of view of the optical cameras during the off-line process as well as the on-line process (called the patient run); and apparatus for computing a respective projection matrix from an image provided by any of the X-ray source and detector, and the optical cameras. A method to obtain the projection matrices characterizing the X-ray imaging geometry during the patient run, using the projection matrices associated to X-ray geometry as well as the optical cameras computed during an off-line process, and the projection matrices associated to the optical cameras during the patient run. The relative motion of the apparatus between the off-line and on-line process is computed using the projection matrices characterizing the imaging geometry of the optical cameras. This information leads us to the modification of the off-line estimation of X-ray imaging geometry and to the characterization of its on line imaging geometry.

30 Claims, 12 Drawing Sheets

METHOD AND APPARATUS FOR CALIBRATING AN INTRA-OPERATIVE X-RAY SYSTEM

The present invention relates to X-ray systems and, more particularly, to the calibration of intra-operative X-ray systems.

The X-ray fluoroscope is a widely available, low cost two-dimensional (2D) imaging equipment. Multiple views are possible, and typically this is done by turning the arm of a fluoroscope, such as a C-arm fluoroscope, an example of which is shown in FIG. 1a and FIG. 1b.

Particular problems arise in the calibration of mobile intra-operative X-ray systems in the case where 3D reconstruction is to be performed. In the prior art, simple systems such as a mobile C-arm system have not generally been utilized for 3D reconstruction. In order to do a 3D reconstruction, the X-ray projection geometry needs typically to be characterized during the patient run. Such systems are generally relatively inexpensively constructed and typically lack the required stability and reproducibility. Therefore, the calibration needs to be done each time during the patient run since there is insufficient repeatability to apply simply the results of an off-line calibration.

The definitions and constraints involved in this type of application render the use of a calibration phantom X-ray operation impracticable. Thus, use of a phantom of X-ray opaque material is not practical because the phantom will interfere with the region of interest being viewed by the physician. If a calibration ring is used in conjunction with a limited region of interest such as the brain it may be used on an adjacent body part, such as the neck, without interfering with the part of interest, whereas in the case of a major body part such as the torso, this is no longer practicable.

Furthermore, if a calibration ring is used in a large machine, the projection in a relatively parallel radiation path will cover a smaller portion of the detector surface, whereas in a small machine, the projection will be more divergent and will spread over a larger part of the detector surface and thereby interfere with the viewing of a region of interest.

In the event that sufficient stability exists to provide repeatability between two consecutive runs, one with the calibration device and the patient and a second run with only the patient, the requirement of exposing the patient to a double dosage of radiation is herein recognized as not being acceptable.

In accordance with an aspect of the invention, a method for calibrating an intra-operative X-ray system having an X-ray source and a detector, the method comprises the steps of:

(1) performing an off-line process comprising:
 (a) initializing the X-ray system into an arbitrary position,
 (b) placing into a position an X-ray phantom,
 (c) placing into a first position an optical phantom,
 (d) taking a radiographic image,
 (e) taking an optical image by a camera associated with the X-ray source,
 (f) taking an optical image by a camera associated with the detector; and
(2) performing an on-line process comprising:
 (A) initializing the X-ray system into a position,
 (B) placing into a second position the optical phantom,
 (C) taking a radiographic image,
 (D) taking an optical image by a camera associated with the X-ray source,
 (E) taking an optical image by a camera associated with the detector.

(3) combining information from the off-line optical images and X-ray image and the on-line optical images so as to derive a projection matrix for use in an image reconstruction process using the on-line X-ray image.

In accordance with an aspect of the invention, the second position of the optical phantom in step 2-(B) is the same as the first position of the optical phantom in step 1-(c).

In accordance with an aspect of the invention, the second position of the optical phantom in step 2-(B) is displaced from the first position of the optical phantom in step 1-(c).

In accordance with an aspect of the invention, a method for calibrating an intra-operative X-ray system includes a step of determining spatial relationship parameters of the first position of the optical phantom relative to the second position of the optical phantom.

In accordance with an aspect of the invention, apparatus for calibrating an intra-operative X-ray system having an X-ray source and a detector comprises:
 an optical camera associated with the X-ray source;
 an optical camera associated with the detector;
 an X-ray phantom placed within a field of view of the X-ray system;
 an optical phantom placed within a field of view of the optical cameras; and apparatus for computing a respective projection matrix from an image provided by any of the X-ray source and detector, and the optical cameras.

In accordance with an aspect of the invention, a method for calibrating an intra-operative X-ray having an X-ray source and a detector system during a rotational run around a patient, comprises the steps of: beginning at a starting position and taking a radiographic image of an X-ray phantom from a first spatial position and taking respective optical images of an optical phantom from respective second and third spatial positions, the first and second spatial positions being in fixed relationship relative to the first spatial position, wherein the optical and X-ray phantoms are in fixed spatial relationship to one another; and deriving and storing respective projection matrices from the images.

In accordance with an aspect of the invention, the steps are repeated up to an end position of the run.

In accordance with an aspect of the invention, the steps are performed without a patient being present.

In accordance with an aspect of the invention, a method for calibrating an intra-operative X-ray comprises the following steps with a patient being present: beginning at the starting position and taking respective optical images of the optical phantom from the first and second spatial positions in fixed relationship relative to the first spatial position; deriving respective projection matrices from the images; and calculating an X-ray projection matrix from the projection matrices.

In accordance with an aspect of the invention, the steps performed with the patient being present are performed without the X-ray phantom being present.

In accordance with an aspect of the invention, apparatus for calibrating an intra-operative X-ray system having an X-ray source and a detector includes an optical camera associated with the X-ray source includes an optical camera associated with the detector; an X-ray phantom placed within a field of view of the X-ray system during an off-line process; an optical phantom placed within a field of view of the optical cameras during the off-line process as well as the on-line process (called the patient run); and apparatus for computing a respective projection matrix from an image provided by any of the X-ray source and detector, and the optical cameras. A method to obtain the projection matrices characterizing the X-ray imaging geometry during the patient run, using the projection matrices associated to X-ray geometry as well as the optical cameras computed during an off-line process, and the projection matrices associated to the optical cameras during the patient run. The relative motion of the apparatus between the off-line and on-line process is computed using the projection matrices characterizing the imaging geometry of the optical cameras. This information leads us to the modification of the off-line estimation of X-ray imaging geometry and to the characterization of its on line imaging geometry.

In accordance with an aspect of the invention, a method for calibrating an intra-operative X-ray having an X-ray source and a detector system during a rotational run around a patient, the method comprising the steps of: beginning at a starting position and taking a radiographic image of an X-ray phantom from a first spatial position and taking respective optical images of an optical phantom from respective second and third spatial positions, the first and second spatial positions being in known relationship relative to the first spatial position, wherein the optical and X-ray phantoms are in known spatial relationship to one another; and deriving and storing respective projection matrices from the images.

In accordance with an aspect of the invention, a method for calibrating an intra-operative X-ray comprises the following steps with a patient being present: beginning at the starting position and taking respective optical images of the optical phantom from the first and second spatial positions in known relationship relative to the first spatial position; deriving respective projection matrices from the images; calculating an X-ray projection matrix from the projection matrices and from the known relationships recited in claim 23.

The invention will be more fully understood from the detailed description of preferred embodiments which follows, in conjunction with the drawing, in which FIGS. 1A and B show a mobile intra-operative X-ray system showing the position of an X-ray source s and a detector plane d;

Figure 1:
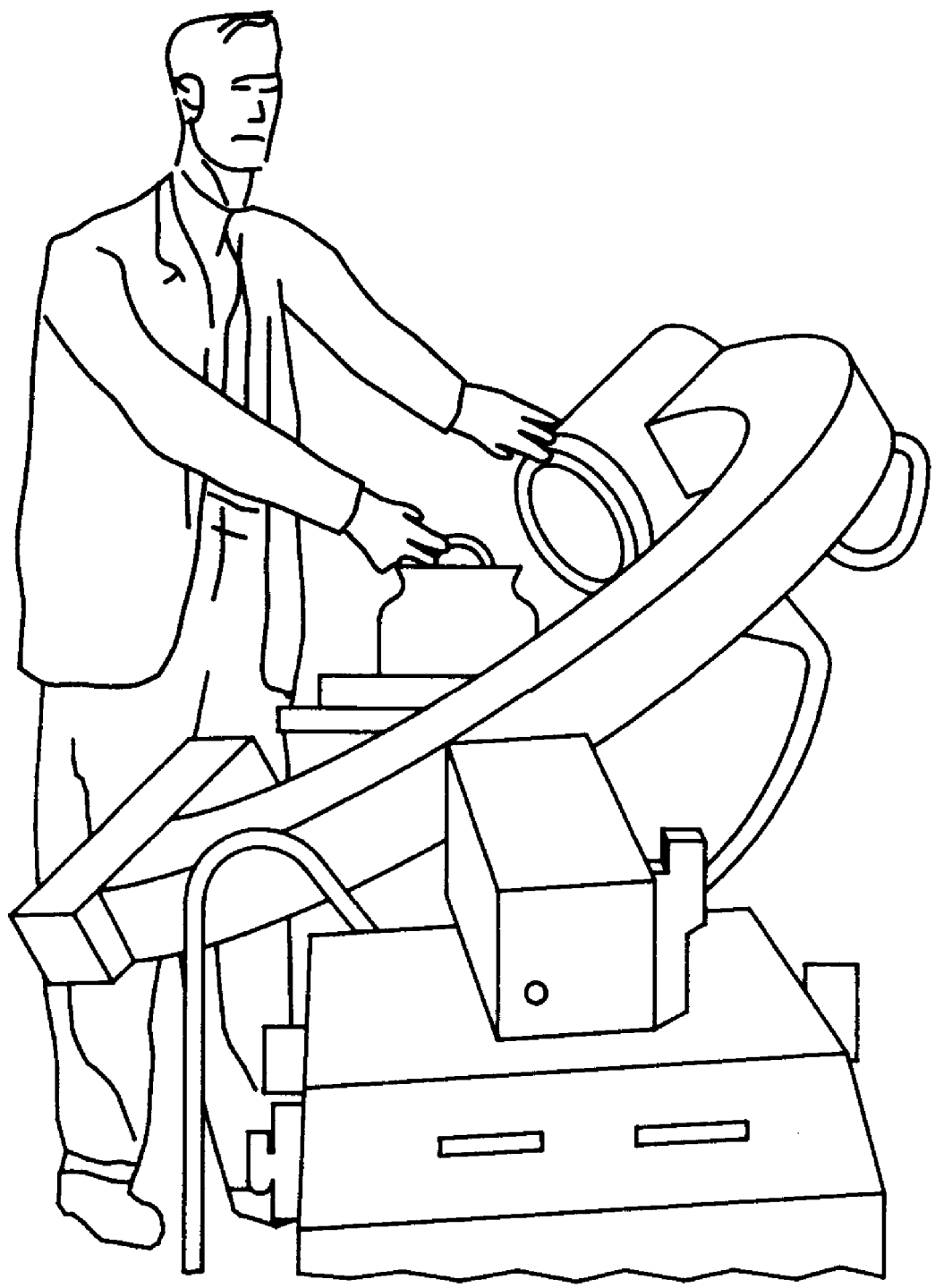
Figure 1B:
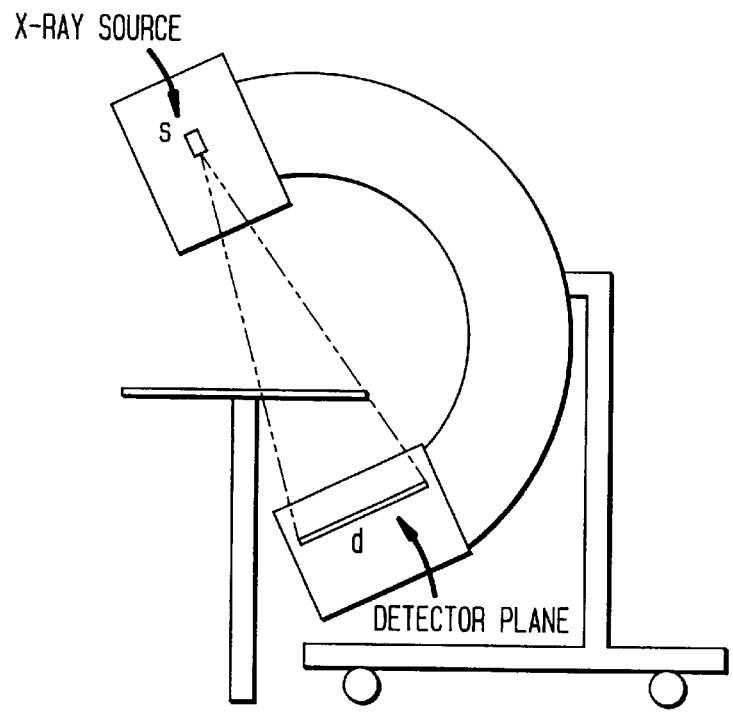
Figure 2:
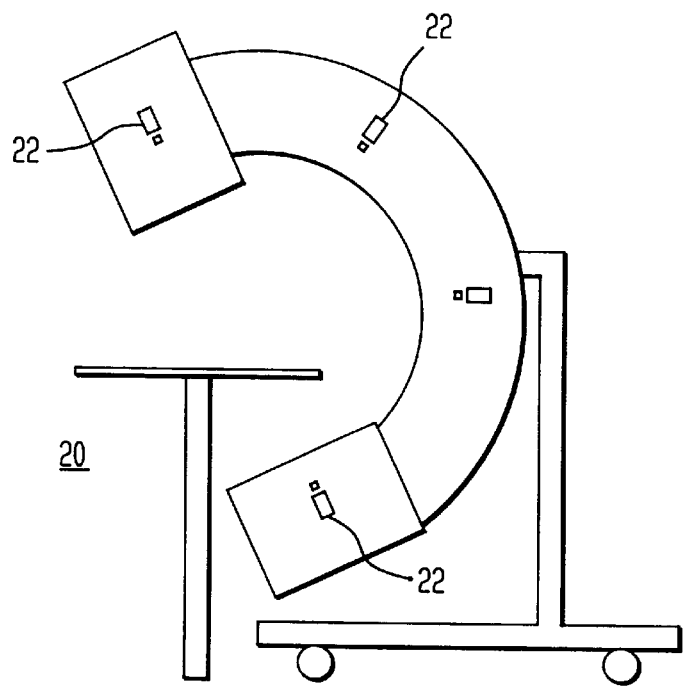
FIG. 2 shows cameras mounted on an X-ray C-arm in accordance with the invention.

In accordance with an embodiment of the invention shown in FIG. 2, optical cameras 22 of an X-ray unit 20 are attached to the mobile C-arm in spatially fixed relationship thereto. The number of cameras to be used is determined by the requirement of attaching a camera to each moving part of the X-ray system which plays a role in the geometrical configuration of the imaging process. For example, if the X-ray source and the detector were capable of independent motion, a camera is attached to each.

The spatial relationship between the cameras and the X-ray imaging portions of the apparatus are primarily determined by the C-arm structure acting as unit, rather than by the support bearings and the frame or trunnion parts. Accordingly, this spatial relationship is sufficiently stable that it can be depended upon not to vary significantly over a certain period of use.

In accordance with an embodiment of the invention, a registration procedure is first carried out, in which an "off-line" calibration, without a patient being present, is performed, that is, one or more static pictures are taken by each camera and, at the same time, an X-ray radiographic picture is taken from an intelligent phantom with multiple characteristics. See FIG. 4.

Figure 3:
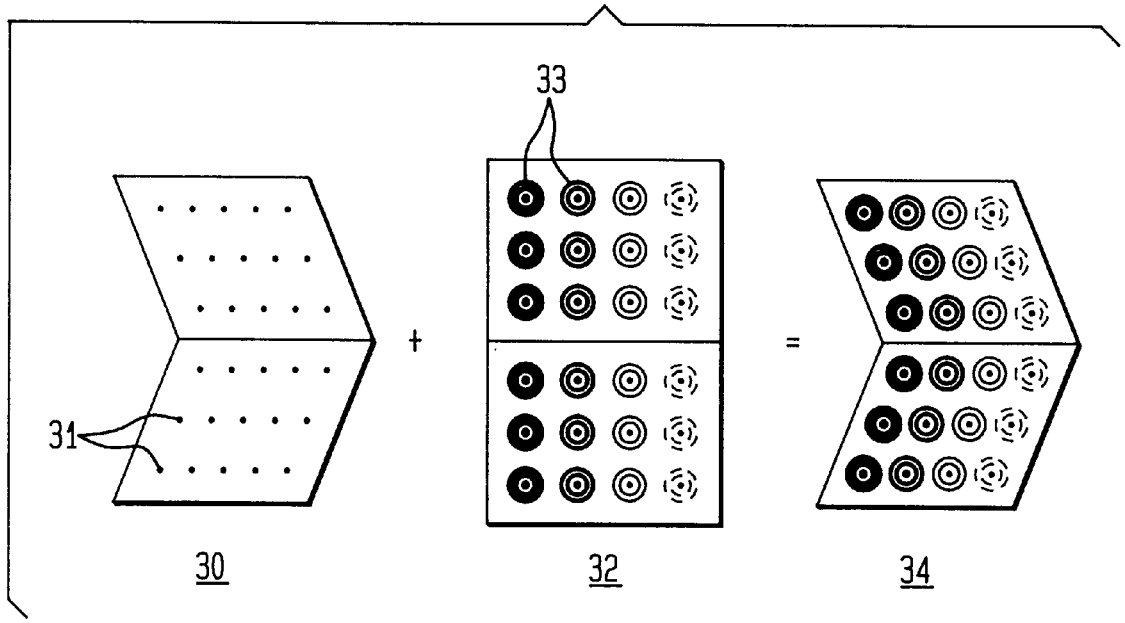
FIGS. 3–6 show various phantom arrangements in accordance with the invention.

The exemplary phantom shown in FIG. 3 comprises two parts: one part 30 is adapted to the X-ray imaging modality, and the other part 32 is adapted to the optical cameras. Markers, such as steel balls 31 or other elements with a high X-ray absorption coefficient, are utilized in an X-ray target for the X-ray picture. Optical targets 33, exhibiting easily read, well-defined patterns printed on X-ray-transparent material are provided for the optical cameras. The illustrative example of FIG. 3 not especially adapted to any particular imaging geometry. The calibration phantom for the optical cameras can be one of a number of readily available materials selected for X-ray transparency and compatibility with an operating room environment.

Figure 4:
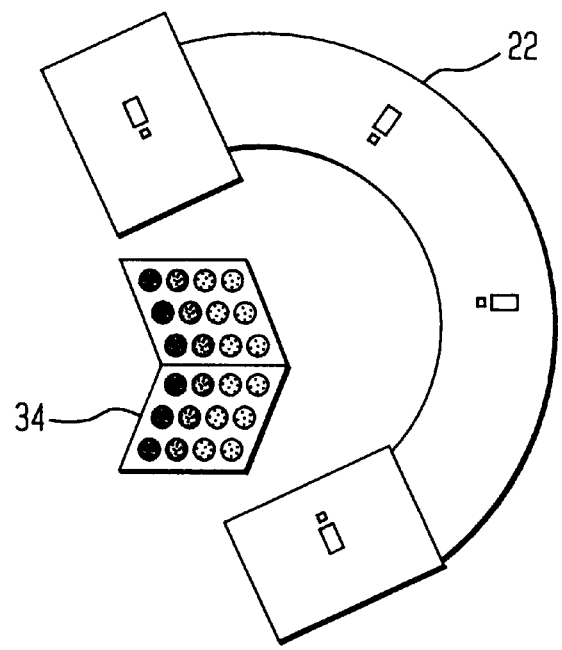

The mechanically coupled camera imaging system and the X-ray imaging system, as shown in FIG. 4, for example, are then calibrated to the same world coordinate system. Owing to the stability of the relationship between the camera and X-ray imaging systems, a transformation from the camera's coordinate system and the X-ray imaging system coordinates is accurately and dependably computed.

Figure 5:
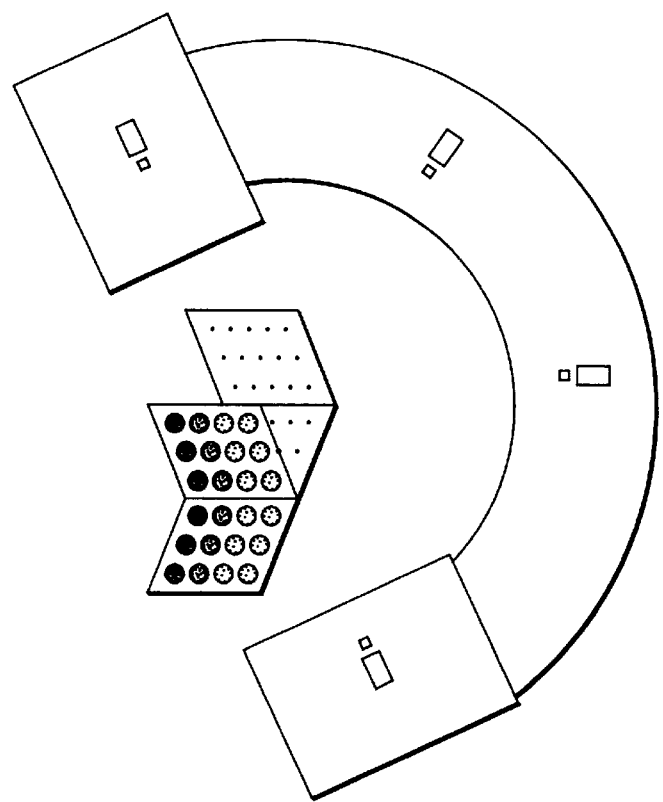
Figure 6:
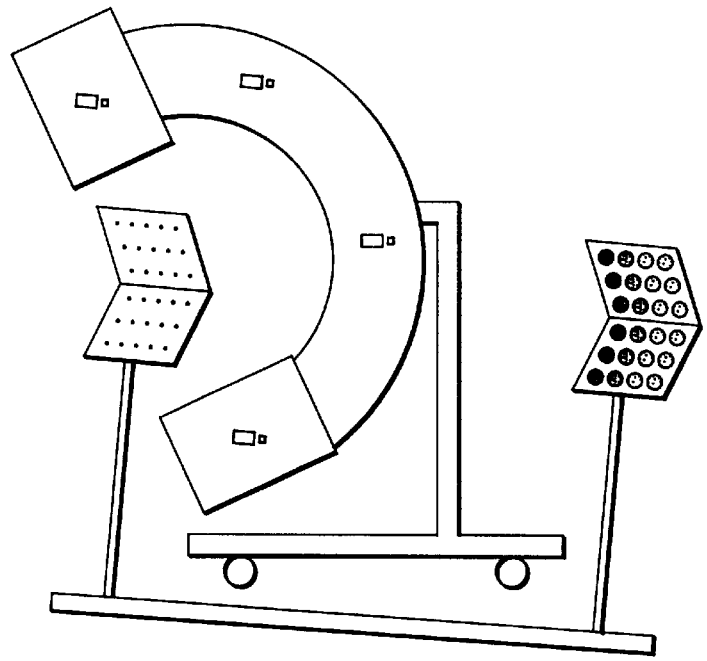

It is noted that the respective calibration phantoms in accordance with the invention, one for the cameras and one for the X-ray, do not have to be superimposed: They need only have a well-defined position relative to each other. This is illustrated by examples shown in FIGS. 5 and 6. FIG. 5 shows that the respective phantoms are juxtaposed and FIG. 6 shows that they are relatively spaced wide apart. Furthermore, once the cameras and the X-ray system are calibrated, it is not necessary to have the same phantoms in the operating room, where the patient is present. Because the X-ray/optical camera relationship has been defined and recorded, only a simple optical phantom is now needed for the optical cameras.

It is particularly noted that the optical cameras in accordance with the invention do not necessarily have to have the patient in view or even the patient's bed: they can look away from that direction and still serve their intended purpose. In this case, the off-line calibration phantom is somewhat more complicated but, since it is only required occasionally for the registration procedure at which time, the patient being absent, there is generally no difficulty with the space and time needed for the off-line calibration.

Figure 7:
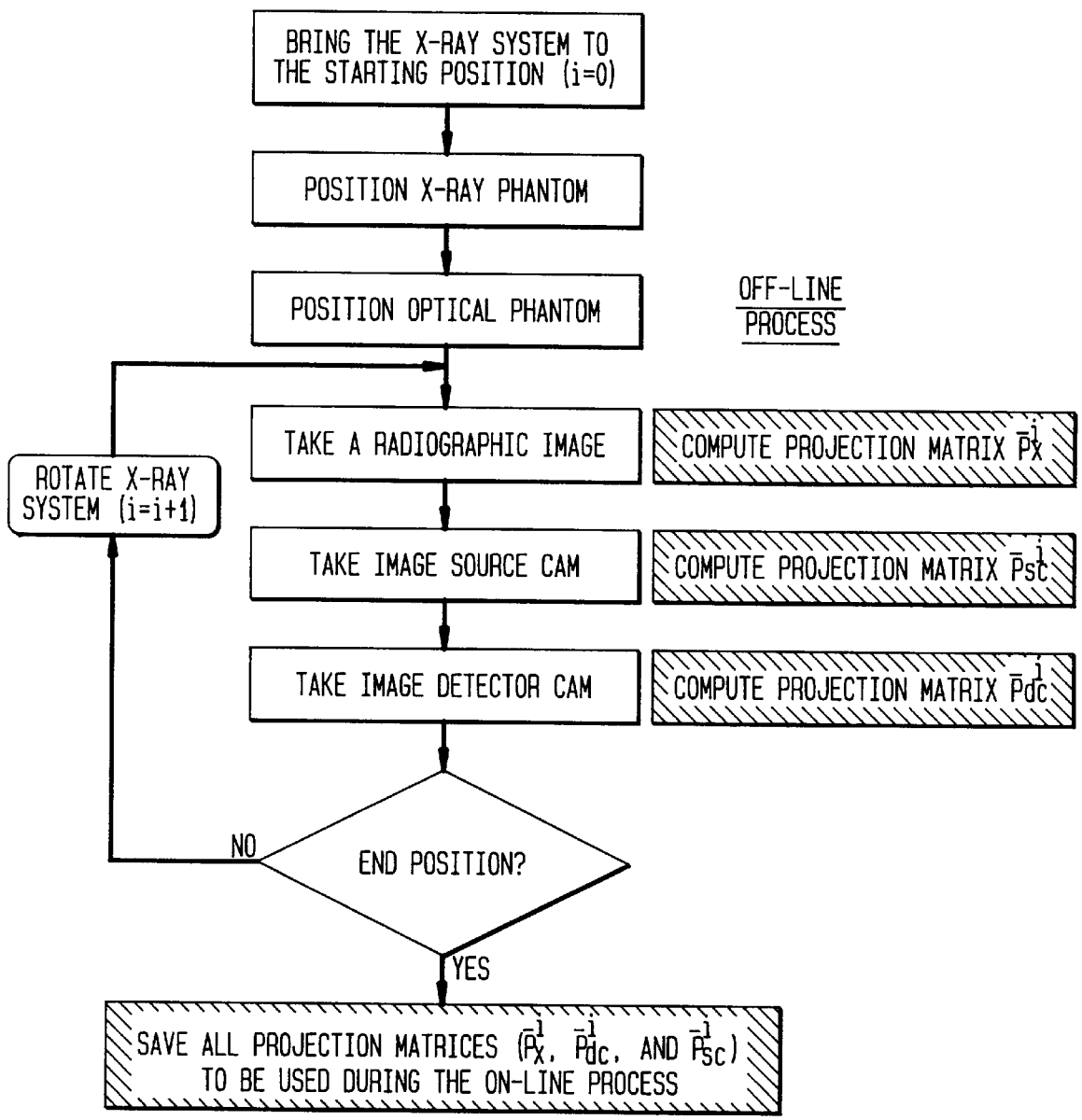
FIGS. 7 and 9 show flow charts helpful to a fuller understanding of the invention.

The motion of the cameras and/or associated projection matrices is determined and, utilizing the results obtained in the off-line calibration procedure, the parameters of the moving X-ray system are deducted. An example of off-line X-ray/cameras calibration in this case is illustrated by the Flowchart in FIG. 7.

The steps of the method in accordance with the invention can be stated as follows.

Initial off-line calibration: The C-arm is put through a motion resembling as closely as possible the motion it is expected to have during the patient run. Two calibration phantoms are located in the field of view. The first calibration phantom comprises a set of markers intended to be clearly apparent on the X-ray image, such as a set of steel balls, preferably in a matrix carrier which is itself relatively transparent to X-rays.

The second calibration phantom exhibits visual patterns which can be well detected, identified, and precisely located on the images taken by the optical cameras. Conveniently, the optical cameras are in the form of charge coupled device (CCD) optical wavelength cameras, though this is by no means essential.

Figure 8:
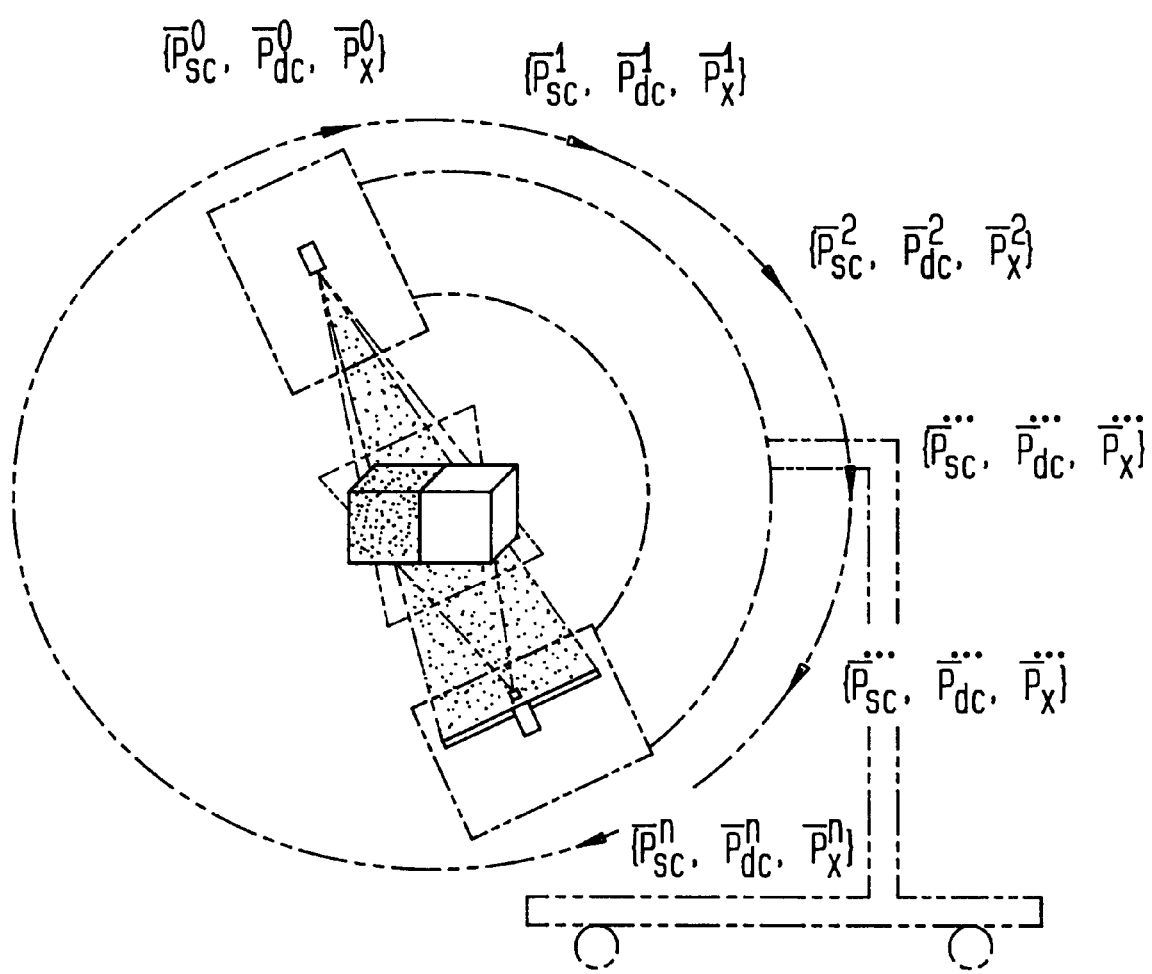
FIGS. 8 and 10 show diagrammatic representations of an estimation of projection matrices in accordance with the invention.

The correspondence found between three dimensional (3D) model points on the optical calibration phantoms and their X-ray images, as well as their CCD camera images is utilized to estimate three sets of projection matrices, defining the projection geometry of the X-ray equipment and of the CCD cameras. This initial off-line calibration process is found in FIG. 8.

On-line calibration: only optical phantoms are utilized during the patient run. No X-ray marker or phantom is used, in order to provide as much unobstructed viewing as possible for the operating physician. Optionally, the optical phantoms can be placed in respective new positions, if this is desirable because it is more appropriate for the actual medical procedure or intervention to be performed. It is however necessary that these new positions for the optical phantoms be accurately defined with respect to the respective phantom positions that were utilized during the off-line calibration process. This relationship is purely geometric/mechanical and can be readily established, particularly since the whole of such a procedure is carried out with no patient present and before any on-line calibration takes place.

Figure 9:
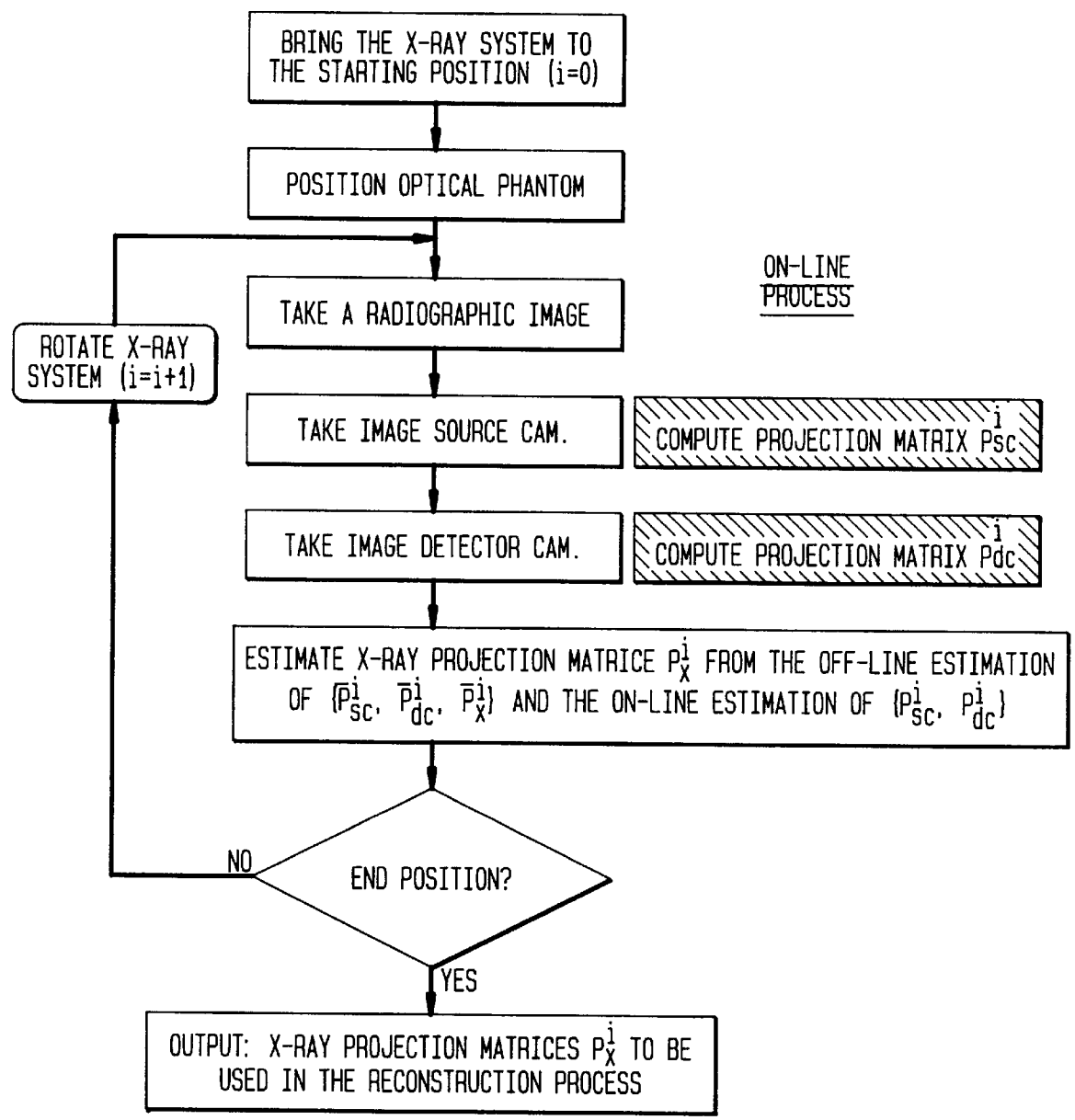
Figure 10:
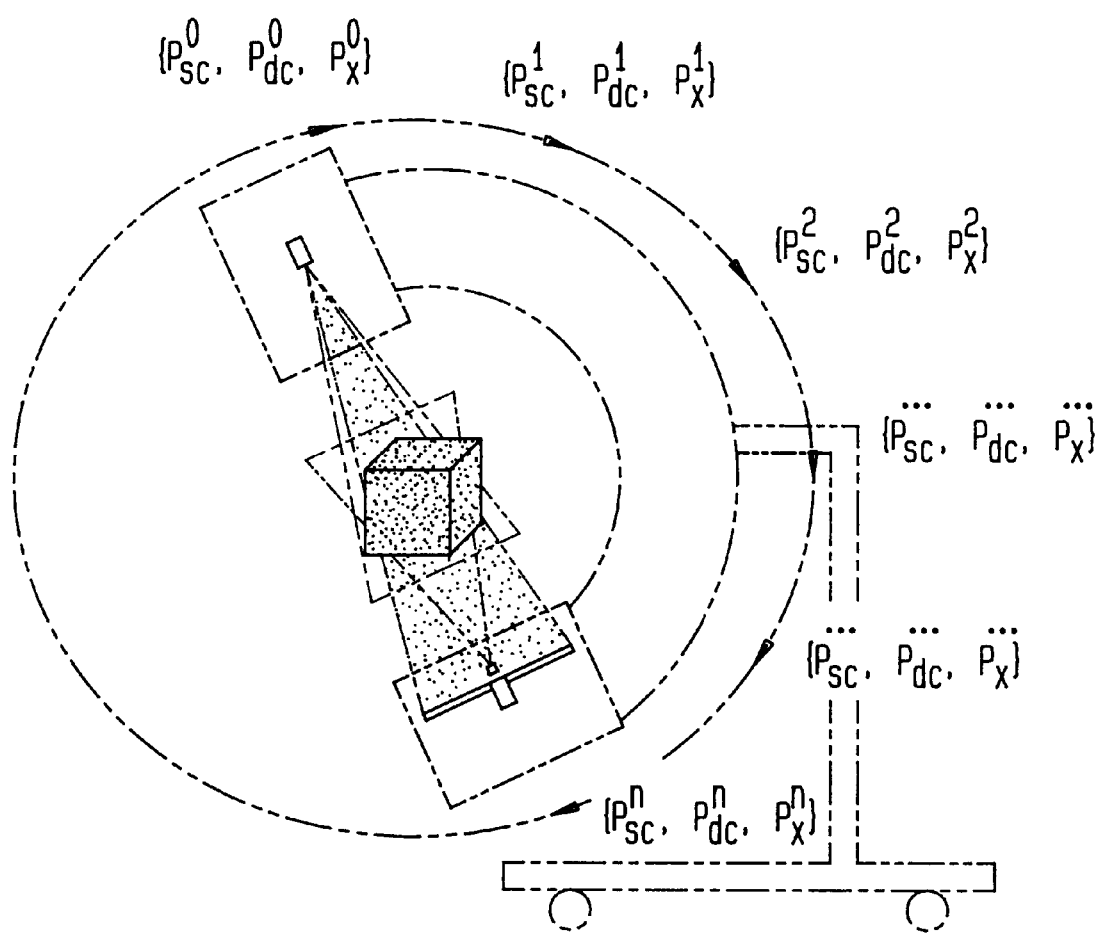

During the patient run, a computation is carried out of the projection geometry of the CCD cameras and the X-ray projection geometry is deducted. The flowchart of FIG. 9 illustrates an example of the on-line calibration process. FIG. 10 illustrates the nature of the problem to be solved during the on-line calibration process.

Figure 11:
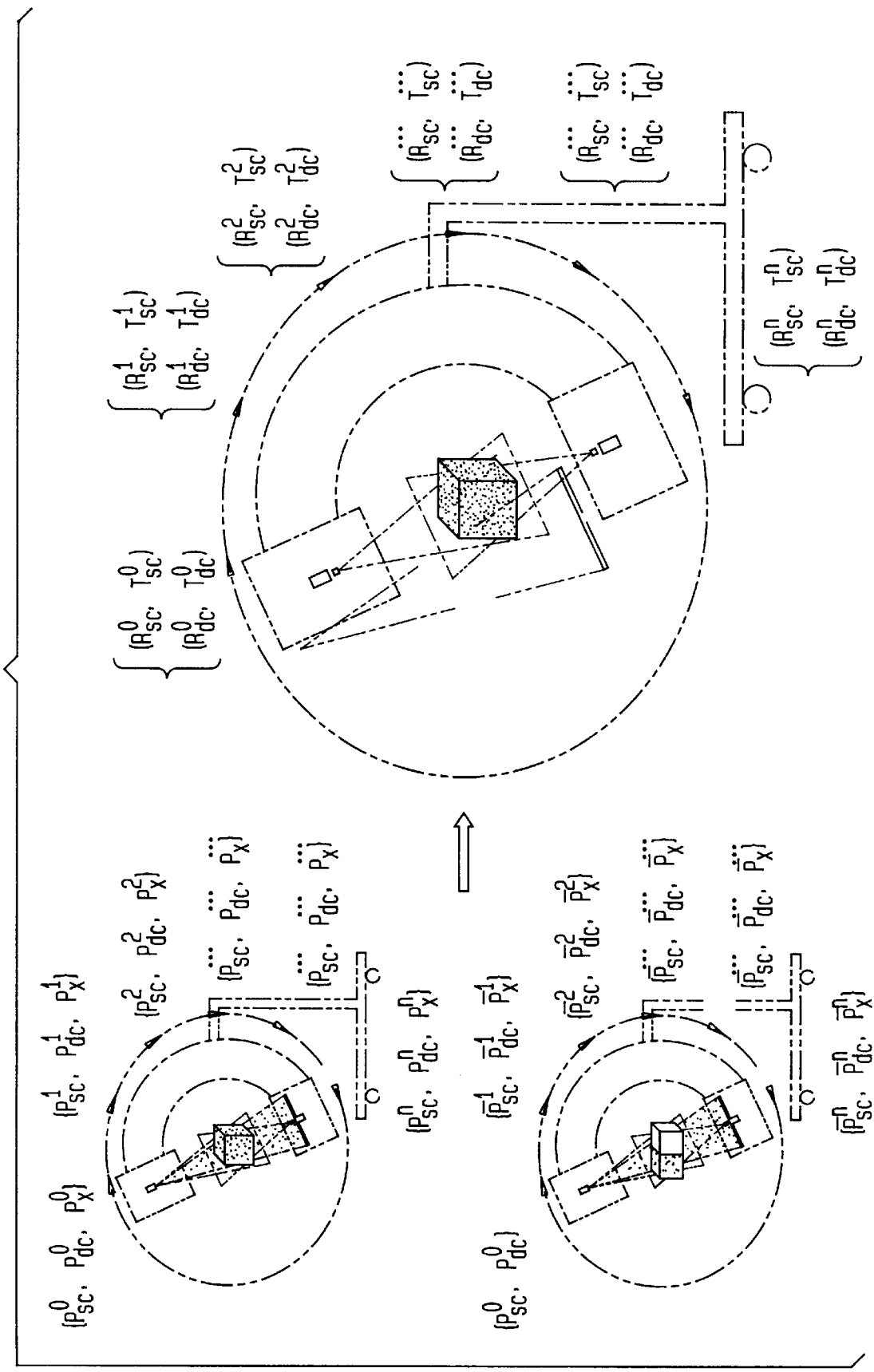
FIG. 11 shows a diagrammatic representation of a computation of relative motion between two sequences in accordance with the invention.

In order to estimate the patient run X-ray projection matrices, first the relative motion of each optical camera between the off-line calibration and the patient run is computed. See FIG. 11.

In order to compute the projection matrix from the image of a calibration phantom, known patterns on the calibration phantom are automatically detected on the image. The correspondences between these patterns and the 3D model of the calibration phantom is then established. This is done by choosing the patterns such that their images can be uniquely identified. Once the correspondences between points on the model, such as the centroid of a pattern, and their images are established, the projection matrix is computed by solving the homogeneous system of equations $P*Mi=\lambda i*mi$, $i=1 \ldots N$, for the elements of the 3×4 projection matrix P. In this equation N is then number of point correspondences, Mi, $i=1 \ldots N$, are the homogeneous coordinates of N 3D points on the model, and mi, $i=1 \ldots N$, the homogeneous coordinates of their corresponding image points. In the case of radiographic imaging process the pattern should be composed of parts opaque to the X-ray such as steel balls, while in the case of imaging by optical cameras these are visual patterns such as precisely drawn circles in color, or in black and white.

In the following, parameters relating to the camera attached by the X-ray source are designated by "sc" (source camera) and parameters relating to the camera attached by the detector plane are designated by "dc" (detector camera).

The details of the motion estimation are as follows, showing the direct computation of motion from projection matrices. The present mathematical method allows computation of the motion of the imaging device using the 3×4 projection matrices $P^i$, and $P^j$, computed before and after a movement of the imaging device.

The 3×3 matrix p13 and the 3-D vector p4 are defined such that P=[p13 p4]. The projection matrix can be written in terms of a rotation matrix R defining the orientation of the camera, a translational vector T, and a upper triangular matrix A defining the camera intrinsic parameters (see the book of O. D. Faugeras referenced below). Thus, p13=AR and p4=AT.

If the imaging parameters stay constant during the C-arm motion, it is herein shown that the motion of the C-arm can be also computed without the decompostion of the projection matrices. In the application particular to the described embodiment of the invention, the distortion correction process, which precedes the calibration measurement, automatically forces the imaging parameters to stay constant. If $P^i$ and $P^j$ are the projection matrices obtained at two arbitrary position of the C-arm. The motion of the C-arm (R(i,j), T(i,j)), and the two projection matrices satisfy the following equation:

$$P^j = \kappa P^i \begin{bmatrix} R_{(i,j)} & T_{(i,j)} \\ O^t & 1 \end{bmatrix} \quad (1)$$

C-arm motion can therefore be directly computed:

$$R_{(i,j)} = \kappa p_{13}^{i^{-1}} p_{13}^j \text{ and } T_{(i,j)} = p_{13}^{i^{-1}}(\kappa p_4^j - p_4^i)$$

There are two main difficulties for accurately computing the unknowns R(i,j), T(i,j) and κ. The first one is the fact that the matrix R(i,j) is a rotation matrix. This means that the nine unknowns of the matrix R(i,j) are non-linear functions of the three rotation parameters. The quarternion representation of the rotation matrices is used in order to reduce the number of unknowns and get accurate results. The quarternion has been used in the past in order to solve problems of the form Rv=v'=v', where v and v' are known three dimensional vectors. The second problem here is that the unknown scalar κ makes our equations of the form: Rv=κv'. It is however herein shown that the quarternion representation can still be used in order to accurately compute the rotation matrix R.

It is desired to solve the algebraic equation:

$$R_{(i,j)} p_{13}^i = \kappa p_{13}^j$$

in order to recover the rotation matrix R(i,j) and the scale factor κ. Note that here R(i,j) is the transposed of previously defined p13 the left 3×3 block of the projection matrice. For the simplicity the transposed sign is not utilized. The mathematical equations have exactly the same forms. This expression can be written as:

$$R_{(i,j)} p_1^i = \kappa p_1^u$$

$$R_{(i,j)} p_2^i = \kappa p_2^u$$

$$R_{(i,j)} p_3^i = \kappa p_3^u$$

where $p_k^i$ and $p_k^u$ and the kth columns of the matrices $p_{13}^i$ and $p_{13}^j$. The solution is then given by the rotation matrix which minimizes the following criterion:

$$\text{Min} \sum_{k=1}^{3} \left\| R_{(i,j)} p_k^i - \kappa p_k^j \right\|^2$$

Quarternion representation of rotation matrix has been used to solve this minimization problem where $\kappa=1$, f.g. see [1]. Since similar equations are herein used, there follows a brief definition of define quarternion q, and multiplication x of two quarternions q and q'.

A quarternion can be considered as a pair $[\alpha,\lambda]$, where $\alpha$ is a real number and $\lambda$ a three-dimensional vector. A rotation of angle $\theta$ around the axis u can then represented by the quarternion:

$$\left[\alpha = \cos\left(\frac{\Theta}{2}\right), \lambda = \sin\left(\frac{\Theta}{2}\right)u\right]$$

The multiplication x of two quarternions q and q' is defined as follows:

$$q \times q' = [\alpha\alpha' - \lambda.\lambda', \alpha\lambda' + \alpha'\lambda + \lambda\Lambda\lambda']$$

where $\Lambda$ is the operator for three dimensional crossproduct. The multiplication x is associative but not commutative. The conjugate and the magnitude of a quarternion q are defined as follows:

$$\bar{q} = [\alpha, -\lambda]$$

$$\|q\|^2 = q \times \bar{q} = [\alpha^2 + \|\lambda\|^2, 0] = [\|q\|^2, 0]$$

Note that the scalar value a is here identified with the quarternion $[\alpha,0]$.

The rotation matrix R represented by a unit quarternion $q=[\alpha,\lambda]$ can be written as:

$$\begin{bmatrix} \alpha^2 + \lambda_1^2 - \lambda_2^2 - \lambda_3^2 & 2\lambda_1\lambda_2 - 2\alpha\lambda_3 & 2\lambda_1\lambda_3 - 2\alpha\lambda_2 \\ 2\lambda_1\lambda_2 - 2\alpha\lambda_3 & \alpha^2 + \lambda_1^2 - \lambda_3^2 - \lambda_3^2 & 2\lambda_2\lambda_3 - 2\alpha\lambda_1 \\ 2\lambda_1\lambda_3 - 2\alpha\lambda_2 & 2\lambda_2\lambda_3 - 2\alpha\lambda_1 & \alpha^2 + \lambda_1^2 - \lambda_2^2 - \lambda_3^2 \end{bmatrix}$$

It is now important to note that applying the rotation R to a three-dimensional vector v, Rv, can be identified as the product of quarternions:

$$Rv = q \times v \times \bar{q}$$

Note that the three-dimensional vector v is here identified with the quarternion $[0,v]$. Now we can restate the minimization problem of (2) in quarternion notation as:

$$\text{Min} \sum_{k=1}^{3} \left\| p_k^i - kq \times p_k^j \times \bar{q} \right\|^2, \text{ with } \|q\| = 1$$

By multiplying each term of the above equation with $\|q\|^2$, we get:

$$\text{Min} \sum_{k=1}^{3} \left\| p_k^i \times q - kq \times p_k^j \right\|^2, \text{ with } \|q\| = 1$$

There exists a matrix Sk such that:

$$p_k^i \times q - \kappa q \times p_k^j = S_k q$$

where:

$$S_k \begin{bmatrix} 0 & (\kappa p_k^j - p_k^i)^T \\ -(\kappa p_k^u - p_k^i) & (\kappa p_k^u + p_k^i) \end{bmatrix}$$

Equation (3) can then be restated as:

$$\text{Min} \sum_{k=1}^{3} q S_k^T S_k q = \text{Min} q^T S q \quad (4)$$

where $$S = \sum_{k=1}^{3} S_k^T S_k, \text{ and } \|q\| = 1.$$

S is a symmetric matrix and for each constant $\kappa(\neq 0)$ the solution to this problem is the eigenvector $q_{min}^s$ associated with the smallest eigenvalue of S. We however show that the eigenvectors of the matrix S are independent of $\kappa(\neq 0)$. We also show that the eigenvector associated to the smallest eigenvalue stays the same when $\kappa(\neq 0)$ varies.

The rotation matrix R(i,j), and the scalar factor $\kappa$ are then easily deducted.

Looking more closely at $$S_k^T S_k = -S_k^2:$$

$$-S_k^2 = \begin{bmatrix} a_k & b_k^T \\ b_k & c_k \end{bmatrix}$$

where $$a_k = (\kappa p_k^u - p_k^i)^T (\kappa p_k^j - p_k^i())$$

and $$b_k = M(\kappa p_k^u - p_k^i)$$

and $$C_k = (\kappa p_k^u - p_k^i)(\kappa p_k^u - p_k^i)^T - M^2$$

where $M = (\kappa p_k^{j\sim} + p_k^i)$. we then have:

$$a_k = \kappa^2 \|p_k^j\|^2 + \|p_k^i\|^2 - 2\kappa p_k^{jT} p_k^i$$

and $$b_k = (\kappa p_k^j + p_k^i)^\sim (\kappa p_k^j - p_k^i) = (2\kappa (p_k^{i\wedge} p_k^j))$$

and $$C_k = \kappa^2 p_k^j p_k^{jT} - \kappa p_k^i p_k^{jT} - \kappa p_k^j p_k^{iT} + p_k^i p_k^{iT} -$$
$$\kappa^2 p_k^j p_k^{u-} \kappa p_k^i p_k^{jT} - \kappa p_k^u p_k^{jT} - p_k^i p_k^{iT} + \|p_k^i + \kappa p_k^u\|^2 I_{3\times 3}$$
$$= \|p_k^i + \kappa p_k^u\|^2 I_{3\times 3} - 2\kappa (p_k^i p_k^{uT} + p_k^u p_k^{iT})$$

We can therefore write:

$$S_k^t S_k = \alpha_k^2 I_{4\times 4} - 2\kappa Q_k \quad (5)$$

where $\alpha_k = \|p_k^i + \kappa p_k^j\|$, and $$Q_k = \begin{bmatrix} 2p_k^{u^T} p_k^i & (p_k^i \wedge p_k^j)^T \\ (p_k^i \wedge p_k^u) & (p_k^i p_k^{u^T} + p_k^u p_k^{i^T}) \end{bmatrix}$$

now, let us suppose $\lambda I$, $I=1\ldots 4$, are the four eigenvalues of the matrix $S$ and $v_i$, $I=1\ldots 4$, their associated eigenvectors. We have $Sv_i = \lambda_i v_i$. Using equation 5 we have:

$$Sv_i = \sum_{k=1}^{3} S_k^T S_k v_i$$

$$= \sum_{k=1}^{3} \alpha_k^2 v_i - 2\kappa \sum_{k=1}^{3} Q_k v_i$$

This results in ($\kappa \neq 0$):

$$\sum_{k=1}^{3} Q_k v_i = \frac{1}{2\kappa} \left( \sum_{k=1}^{3} \alpha_k^2 - \lambda_i \right) v_i$$

This result shows that the eigenvectors of the matrix S are independent of $\kappa(\neq 0)$. This also shows that the eigenvector associated to the smallest eigenvalue stays the same when $\kappa(\neq 0)$ varies. The rotation matrix R(i,j), and the scalar factor $\kappa$ are then easily deducted. Once the rotation matrix R(i,j) and the scale factor $\kappa$ are computed, the translational vector T(i,j) is computed:

$$T_{(i,j)} = p_{13}^{-1}(\kappa p_4^u - p_4^i)$$

Background material relative to the foregoing can be found in, for example, Z. Zhang and O. Faugeras. 3D Dynamic Scene Analysis: A Stereo Based Approach. Springer, Berlin, Heidelberg, 1992; and O. D. Faugeras. Three-Dimensional Computer Vision: A Geometric Viewpoint. MIT Press, Cambridge, Mass., 1993.

In the case where the system is mechanically stable and where its motion is perfectly reproducible, there should be no motion between the off-line and on-line projection matrices. In this case, in theory, all rotation matrices are 3×3 identity matrices and the translation vectors vanish. So long as this reproducibility is not achieved mechanically, these matrices help provide an estimate of the relative motion between the off-line and the on-line imaging geometry.

Figure 12:
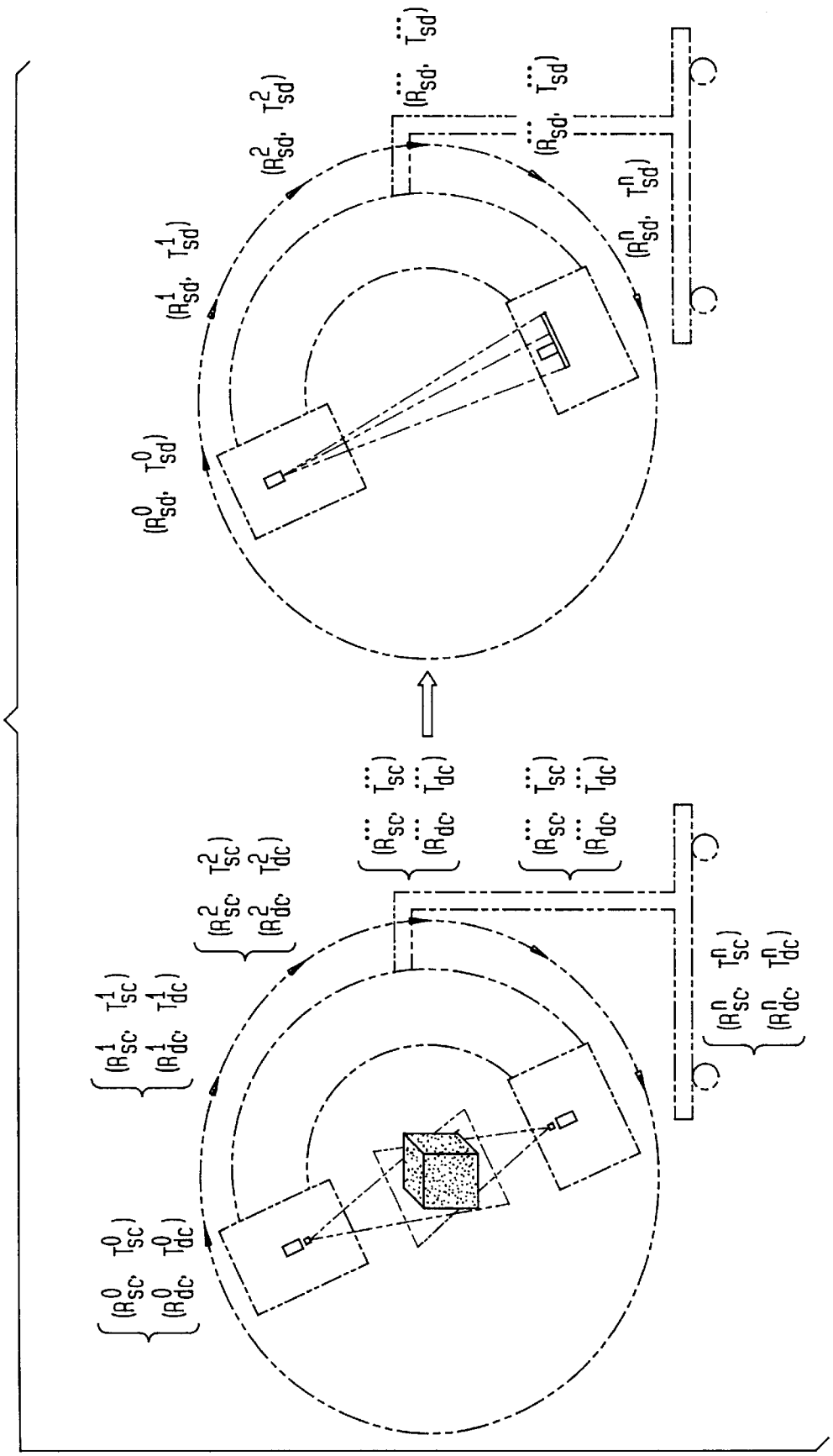
FIG. 12 shows a diagrammatic representation of a computation of relative motion between two cameras in accordance with the invention.
Figure 13:
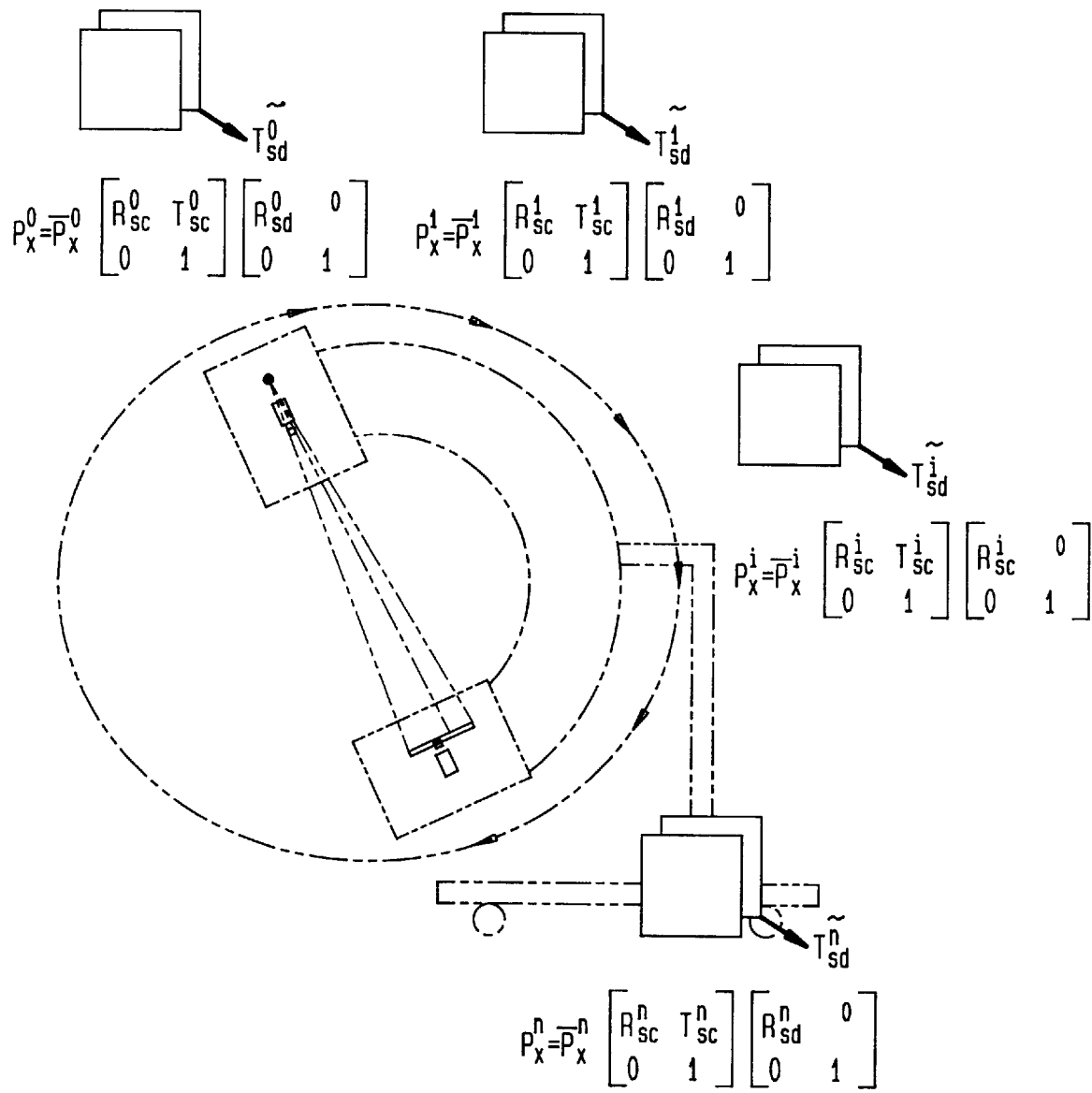
FIG. 13 shows a diagrammatic representation of an estimation of a projection matrix in accordance with the invention.

In the event the detector has well-known characteristics at each position, which is the case when using ASI (Amorphous Silicon) detectors rather than image intensifiers, the changes in the X-ray geometry are due to both the motion of the X-ray source and the detector plane. FIG. 12 shows how the respective motion of each of the optical cameras is used to find their relative motion.

Often a simple pinhole model is used for modelling both the X-ray imaging geometry and the imaging geometry of CCD optical cameras. Such simple modelling has different interpretations in these two cases. One difference is that if the imaging plane of an optical camera is rotated, this will not change the optical axis of the camera which is defined by the lens. Therefore the same pinhole model is kept for the projection geometry and this change is taken account of by changing the intrinsic parameters or by a so-called image warping. In the X-ray geometry there is no lens per se. The optical axis of the pinhole model can be defined by a perpendicular dropped from the source on to the detector plane. Therefore a small rotation of the detector plane can be considered as being equivalent to a global rotation of the whole camera and a rotation can be applied to the pinhole model so as to arrive at a new source/detector geometry.

Relative translation between the X-ray source and the detector as computed from the relative motion of their associated optical cameras also changes the intrinsic image parameters. This cannot be modeled through a global motion of the pinhole model of the X-ray imaging geometry. This motion can be compensated by horizontal and vertical shifts of the image followed by a change of scale. The change in scale is however believed to be negligibly small and thus does not have a measurable effect on image formation. The image correction does use only the horizontal and vertical shift. The symbol "~" is used in Figure K for emphasis. Figure K shows how the projection matrices are estimated during the patient run.

Figure 14:
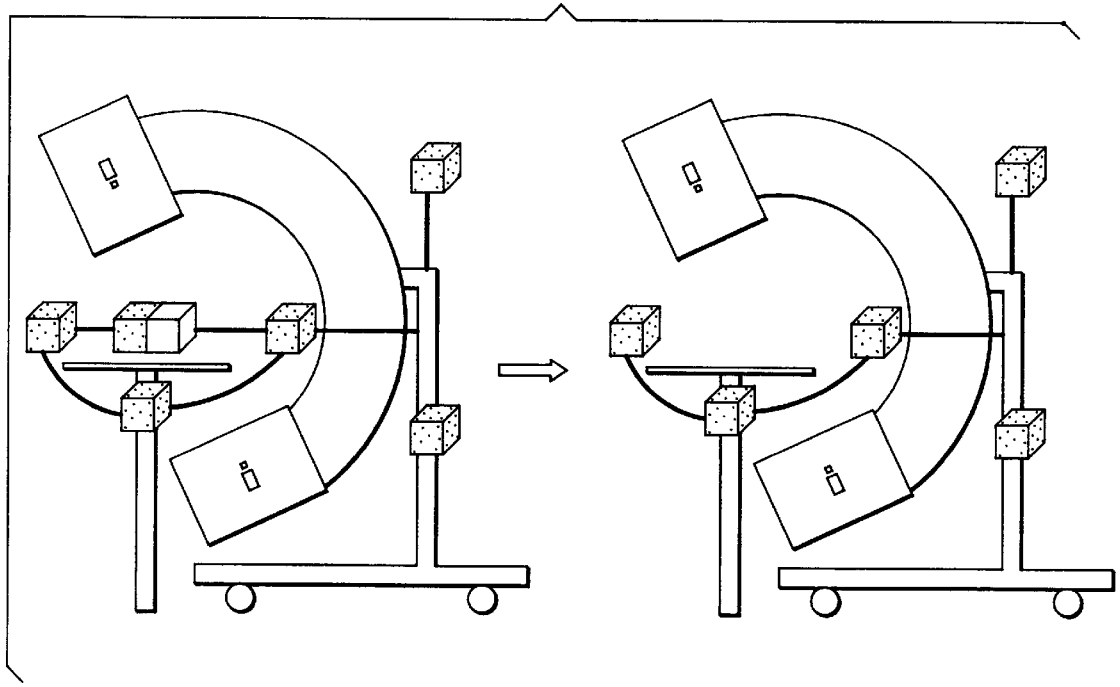
FIG. 14 shows a diagrammatic representation of a method in accordance with the invention.

It is also contemplated that an off-line calibration pattern includes the on-line optical phantoms. FIG. 14 shows one possible arrangement. It is understood that data storage and processing can be performed by a computer.

While the invention has been described by way of exemplary embodiments, it will be apparent to one of skill in the art to which it pertains that a number of changes and substitutions may be made without departing from the spirit of the invention. Such changes and substitutions are within the contemplation of the invention which is defined by the scope of the claims following.

I claim:

1. A method for calibrating an intra-operative X-ray system having an X-ray source and a detector, said method comprising the steps of:
   (1) performing an off-line process comprising:
      (a) initializing said X-ray system into an arbitrary position,
      (b) placing into a position an X-ray phantom,
      (c) placing into a first position an optical phantom,
      (d) taking an off-line X-ray image,
      (e) taking an optical image by a camera associated with said X-ray source,
      (f) taking an off-line optical image by a camera associated with said detector; and
   (2) performing an on-line process comprising:
      (A) initializing said X-ray system into a position,
      (B) placing into a second position said optical phantom,
      (C) taking an on-line X-ray image,
      (D) taking an on-line optical image by a camera associated with said X-ray source, and
      (E) taking an optical image by a camera associated with said detector; and
   (3) combining information from said off-line optical images and said off-line X-ray image and the on-line optical images so as to derive a projection matrix for use in an image reconstruction process using said on-line X-ray image.

2. A method for calibrating an intra-operative X-ray system as recited in claim 1, wherein said second position of said optical phantom in step 2-(B) is the same as said first position of said optical phantom in step 1-(c).

3. A method for calibrating an intra-operative X-ray system as recited in claim 1, wherein said second position of said optical phantom in step 2-(B) is displaced from said first position of said optical phantom in step 1-(c).

4. A method for calibrating an intra-operative X-ray system as recited in claim 3, including a step of determining spatial relationship parameters of said first position of said optical phantom relative to said second position of said optical phantom.

5. A method for calibrating an intra-operative X-ray system as recited in claim 4, wherein step (3) includes combining of said spatial relationship parameters of said first position of said optical phantom so as to derive said projection matrix for use in an image reconstruction process.

6. A method for calibrating an intra-operative X-ray system as recited in claim 1, including a step of utilizing said projection matrix so as to form a reconstructed image.

7. A method for calibrating an intra-operative X-ray having an X-ray source and a detector system, said method comprising the steps of:
(A) performing an off-line process comprising:
(a) initializing said X-ray system into an initial position, as closely as possible to its position when a patient is present,
(b) placing into position an X-ray phantom,
(c) placing into position an optical phantom,
(d) taking off-line, a radiographic image,
(e) computing and storing a projection matrix $P_x$
(f) taking off-line, an optical image by a camera associated with said X-ray source,
(g) computing from said optical image and storing a projection matrix $P_{sc}$
(h) taking off-line, an optical image by a camera associated with said detector, and
(i) computing from said optical image and storing a projection matrix $P_{dc}$; and
(B) performing an on-line process comprising:
(1) placing into position an optical phantom,
(2) taking on-line, a radiographic image,
(3) taking on-line, an optical image by a camera associated with said X-ray source,
(4) computing from said optical image and storing a projection matrix $p_{sc}$
(5) taking on-line, an optical image by a camera associated with said detector,
(7) computing from said optical image and storing a projection matrix $p_{dc}$, and
(8) calculating an X-ray projection matrix $P_x$ from said foregoing matrices $P_x, P_{sc}, P_{dc}, p_{sc}, p_{dc}$.

8. A method for calibrating an intra-operative X-ray having an X-ray source and a detector system during a rotational run around the patient, said method comprising the steps of:
(A) performing an off-line process comprising:
(a) initializing said X-ray system into a starting position (i),
(b) placing into position an X-ray phantom,
(c) placing into position an optical phantom,
(d) taking off-line, a radiographic image,
(e) computing and storing a projection matrix $P_x^i$
(f) taking off-line, an optical image by a camera associated with said X-ray source,
(g) computing from said optical image and storing a projection matrix $P_{sc}^i$
(h) taking off-line, an optical image by a camera associated with said detector,
(i) computing from said optical image and storing a projection matrix $P_{dc}^i$
(j) rotating said X-ray system to the next position (i+1)
(k) repeating steps (d) through (j) unless the end position is reached; and
(B) performing an on-line process comprising:
(1) initializing said X-ray system into said starting position (i),
(2) placing into position an optical phantom,
(3) taking on-line, a radiographic image,
(4) taking on-line, an optical image by a camera associated with said X-ray source,
(5) computing from said optical image and storing a projection matrix $p_{sc}^i$
(6) taking on-line, an optical image by a camera associated with said detector,
(7) computing from said optical image and storing a projection matrix $p_{dc}^i$
(8) calculating an X-ray projection matrix $P_x^i$ from said foregoing matrices $P_x^i, P_{sc}^i, P_{dc}^i, p_{sc}^i, p_{dc}^i$;
(9) rotating said X-ray system tp the next position (i+1),
(10) repeating (3) through (9) unless the end position is reached, and
(11) applying said projection matrices $P_x^i$ to an image reconstruction process.

9. Apparatus for calibrating an intra-operative X-ray system having an X-ray source and a detector, said apparatus comprising:
an optical camera associated with said X-ray source;
an optical camera associated with said detector;
an X-ray phantom placed within a field of view of said X-ray system;
an optical phantom placed within a field of view of said optical cameras; and
means for computing a respective projection matrix from an image provided by any of said X-ray source and detector, and said optical cameras.

10. Apparatus for calibrating an intra-operative X-ray system as recited in claim 8, wherein said optical camera associated with said X-ray source is mounted in fixed spatial relationship with and proximate said X-ray source.

11. Apparatus for calibrating an intra-operative X-ray system as recited in claim 9, wherein said optical camera associated with said detector is mounted in fixed spatial relationship with and proximate said detector.

12. Apparatus for calibrating an intra-operative X-ray system as recited in claim 10, wherein said X-ray phantom comprises X-ray opaque reference bodies supported in an X-ray transparent body.

13. Apparatus for calibrating an intra-operative X-ray system as recited in claim 11, wherein said optical phantom comprises visible reference marks formed on an X-ray transparent body.

14. Apparatus for calibrating an intra-operative X-ray system as recited in claim 12, including means for utilizing said respective projection matrices so as to form a reconstructed image.

15. A method for calibrating an intra-operative X-ray having an X-ray source and a detector system during a rotational run around a patient, said method comprising the steps of:
beginning at a starting position and taking a radiographic image of an X-ray phantom from a first spatial position and taking respective optical images of an optical phantom from respective second and third spatial positions, said first and second spatial positions being in fixed relationship relative to said first spatial position, wherein said optical and X-ray phantoms are in fixed spatial relationship to one another; and
deriving and storing respective projection matrices from said images.

16. A method for calibrating an intra-operative X-ray in accordance with claim 15 wherein said steps are repeated up to an end position of said run.

17. A method for calibrating an intra-operative X-ray in accordance with claim 16 wherein the steps recited in claim 8 are performed without a patient being present.

18. A method for calibrating an intra-operative X-ray in accordance with claim 17, comprising the following steps with a patient being present:

beginning at said starting position and taking respective optical images of said optical phantom from said first and second spatial positions in fixed relationship relative to said first spatial position;

deriving respective projection matrices from said images; and calculating an X-ray projection matrix from said projection matrices.

19. A method for calibrating an intra-operative X-ray in accordance with claim 18 wherein said steps are performed without said X-ray phantom being present.

20. A method for calibrating an intra-operative X-ray in accordance with claim 19 wherein said steps are repeated up to an end position of said run.

21. A method for calibrating an intra-operative X-ray in accordance with claim 20 wherein an X-ray image is taken at each step.

22. A method for calibrating an intra-operative X-ray in accordance with claim 21 wherein said respective X-ray projection matrices for said steps are utilized for calibration of said X-ray image.

23. A method for calibrating an intra-operative X-ray having an X-ray source and a detector system during a rotational run around a patient, said method comprising the steps of:

beginning at a starting position and taking a radiographic image of an X-ray phantom from a first spatial position and taking respective optical images of an optical phantom from respective second and third spatial positions, said first and second spatial positions being in known relationship relative to said first spatial position, wherein said optical and X-ray phantoms are in known spatial relationship to one another; and deriving and storing respective projection matrices from said images.

24. A method for calibrating an intra-operative X-ray in accordance with claim 23 wherein said steps are repeated up to an end position of said run.

25. A method for calibrating an intra-operative X-ray in accordance with claim 24 wherein the steps recited in claim 8 are performed without a patient being present.

26. A method for calibrating an intra-operative X-ray in accordance with claim 25, comprising the following steps with a patient being present:

beginning at said starting position and taking respective optical images of said optical phantom from said first and second spatial positions in known relationship relative to said first spatial position;

deriving respective projection matrices from said images; and calculating an X-ray projection matrix from said projection matrices and from said known relationships recited in claim 23.

27. A method for calibrating an intra-operative X-ray in accordance with claim 26 wherein said steps are performed without said X-ray phantom being present.

28. A method for calibrating an intra-operative X-ray in accordance with claim 27 wherein said steps are repeated up to an end position of said run.

29. A method for calibrating an intra-operative X-ray in accordance with claim 28 wherein an X-ray image is taken at each step.

30. A method for calibrating an intra-operative X-ray in accordance with claim 29 wherein said respective X-ray projection matrices for said steps are utilized for calibration of said X-ray image.

\* \* \* \* \*